United States Patent [19]

Srivastava et al.

[11] Patent Number: 4,533,541

[45] Date of Patent: Aug. 6, 1985

[54] TIN-117M-LABELED STANNIC (SN$^{4+}$) CHELATES

[75] Inventors: Suresh C. Srivastava, Setauket; George E. Meinken, Middle Island; Powell Richards, Bayport, all of N.Y.

[73] Assignee: The United States of America as represented by the United States Department of Energy, Washington, D.C.

[21] Appl. No.: 526,251

[22] Filed: Aug. 25, 1983

[51] Int. Cl.$^3$ .................. A61K 43/00; A61K 49/00; C07F 7/22
[52] U.S. Cl. .................................. 424/1.1; 424/9; 534/10
[58] Field of Search .................. 424/1.1, 9; 260/429.7

[56] References Cited

PUBLICATIONS

Yano et al., Int. J. Appl. Rad. Isot., 24: 319–325 (1973).
Srivastava et al., from *Nuclear Medicine and Biology Advances*, Ed., C. Raynaud, vol. 2, Pergamon Press, 1983, pp. 1635–1638.
Moretti et al., from *Nuclear Medicine and Biology Advances*, vol. 2, Ed., C. Raynaud, Pergamon Press, 1983, pp. 1651–1654.
Woo et al., from Radio Pharmaceuticals II, Soc. of Nucl. Med. 1979, pp. 147–154.
Oster et al., from *Nuclear Medicine and Biology Advances*, vol. 4, Ed., Rayaoud, 1983, pp. 3251–3256.

*Primary Examiner*—Christine M. Nucker
*Attorney, Agent, or Firm*—Margaret C. Bogosian; James W. Weinberger; Judson R. Hightower

[57] ABSTRACT

The radiopharmaceutical reagents of this invention and the class of Tin-117m radiopharmaceuticals are therapeutic and diagnostic agents that incorporate gamma-emitting nuclides that localize in bone after intravenous injection in mammals (mice, rats, dogs, and rabbits). Images reflecting bone structure or function can then be obtained by a scintillation camera that detects the distribution of ionizing radiation emitted by the radioactive agent. Tin-117m-labeled chelates of stannic tin localize almost exclusively in cortical bone. Upon intravenous injection of the reagent, the preferred chelates are phosphonate compounds, preferable, PYP, MDP, EHDP, and DTPA. This class of reagents is therapeutically and diagnostically useful in skeletal scintigraphy and for the radiotherapy of bone tumors and other disorders.

5 Claims, No Drawings

TIN-117M-LABELED STANNIC (SN⁴⁺) CHELATES

BACKGROUND AND GENERAL DESCRIPTION

The U.S. Government has rights to this invention pursuant to Contract No. DE-AC02-76-CH00016, between the U.S. Department of Energy and Associated Universities, Inc.

UTILITY STATEMENT

The radiopharmaceutical reagents of this invention, the class of Tin-117m radiopharmaceuticals are therapeutic and diagnostic agents that incorporate gamma-emitting nuclides that localize in bone after intravenous injection. Images reflecting bone structure or function can then be obtained by a scintillation camera that detects the distribution of ionizing radiation emitted by the radioactive agent.

Radiochemical reagents, by virtue of their radioactive emission, have become a most useful diagnostic and therapeutic tool. Some of these reagents incorporate a gamma-emitting nuclide and localize in a specific organ or bone after intravenous injection. Images reflecting the organ or bone can then be obtained by means of a scintillation camera that detects the distribution of ionizing radiation emitted by the radioactive reagent. The principal radioactive isotope used in diagnostic procedures is technetium-99m. Other clinically important diagnostic isotopes are thallium-201, gallium-67, and iodine-123. All the above are cyclotran-produced. Therapeutic reagents which localize in pathologic tissue include iodine-131 and phosphorus-32 (both are reactor-produced).

In order to be an effective radioactive drug—whether for therapeutic or diagnostic use—the reagent must combine four elements: low toxicity, specific biodistribution, low background radiation (non-target) dose, and radionuclidic emissions compatible with instrumentation. For example, $^{99m}$technetium combines with pyrophosphate to form $^{99m}$TC-PYP, which localizes in the skeleton in general and in areas of hyperactive bone metabolism in particular. Biodistribution of this agent combines rapid, high concentration by target tissue and low uptake by surrounding tissue with rapid blood clearance and urinary excretion of the non-specifically localized radioactive drug. Thus, the amount of localized reagent to resolve the image on scintillation cameras is obtained with minimal radiation dose to the patient.

The present invention consists of a new class of reagents and the method for making and using those reagents. Tin-117m-labeled chelates of stannic tin exhibit all the favorable qualities mentioned above for $^{99m}$TC-PYP. These reagents localize almost exclusively in skeletal tissue (cortical bone) following intravenous administration in various mammals (mice, rats, rabbits, and dogs). Biodistribution for several of the chelates—methylene diphosphonate (MDP), pyrophosphate (PYP), ethylidenehydroxydisodium phosphonate (EHDP), and diethylene-triamine pentaacetic acid (DTPA)—indicates high and unexpected bone uptake of these reagents, high specific affinity of the tin for bone (i.e. localization), favorable half-life and decay characteristics, and delivery of high local radiation doses with low toxicity to the subject animal. Additionally, these reagents are detectable by autoradiography, whole-body scanning, or scintigraphy. The DTPA as well as the phosphonates chelated with tin-117m exhibit the particular advantage of in vivo stability and produce images of high contrast due to high target-to-backgrund ratios. Tin-117m exhibits radionuclidic properties acceptable for clinical and therapeutic use—half-life of 14 days and a a gamma emission of 158 keV photons, 87%, and abundance of low energy auger and conversion electrons. Short radioisotopic half-life is necessary to minimize patient exposure, but cannot be so short as to preclude commercial processing and transport. In addition, a useful radioisotope must yield an abundance of gamma rays that can be imaged with currently-produced cameras. Internal scatter and absorption of low energy gamma emission and sensitivity and resolution constraints imposed by the collimators and electronics of current scintillation cameras limit useful isotopic emission from 50-60 keV to approximately 350 keV.

SPECIFIC DISCLOSURE

Tin-117m was produced by the $^{116}Sn(n,\gamma)^{117m}Sn$ reaction in the high flux reactor at Oak Ridge (ORNL), with a specific activity of 2mCi/mg as the metal. The metal was dissolved in a minimum quantity of conc. HCl in an inert atmosphere and diluted with water to give a stannous chloride solution in 1-4N HCl as desired. Excess ligand (molar ratios ligand to tin=8-40) was added under stirring and the pH adjusted to 4-7 with NaOH. The preferred ligands, or chelates, are DTPA, MDP, PYP, and EHDP. Of these, DTPA is most effective. Aliquots of these solutions were oxidized to stannic complexes by the addition of a tenfold molar excess (over tin) of $H_2O_2$. Radiochemical purity and the oxidation state of tin were checked by various in-vitro methods including paper chromatography, gel filtration, and HPLC. Tissue distribution studies were done in normal BNL mice. All animals were injected with the appropriate radiopharmaceutical intravenously. A number of time periods up to 7 days after injection were used to collect the data.

Comparative studies were conducted using $Sn^{2+}$chloride (pH 2 and 7), $Sn^{4+}$chloride (pH 2), and Sn(2+ and 4+)-labeled chelates (MDP, DTPA, EHDP, and PYP). (See Table 1.) High and unexpected bone uptake of the above compounds, particularly Sn-DTPA, indicates a high specific affinity of tin for bone, despite the chemically diverse ligands. The various compounds, however, show significant differences in blood clearance, excretion, and soft tissue uptake. Specifically, the stannic form (4+) of tin linked to any of the chelates is preferred.

Tissue distribution in mice of Sn(2+ and 4+) chloride (pH 2 and 7), and of the stannous and stannic chelates of MDP, DTPA, PYP, and EHDP is shown in Table 1. Table 2 shows the bone to tissue ratio of these compounds. Stannous compounds show lower bone uptake and much higher blood and total body background. The stannic-chelate compounds, however, particularly with DTPA, exhibit high bone uptake, almost no blood, muscle, kidney or liver background. Furthermore, autoradiographs show that localization occurred on the bone and not in the bone marrow. Tin-117m(II) chloride (with the pH adjusted to 7 before injection) or tin-117m(IV) chloride (pH2) localize almost exclusively in the liver and the RE system. High bone uptake occurs with these preparations, but the blood levels and whole body retention remain high as well.

Radiopharmaceutical, as defined in this application, includes the radiochemicals and radioactive drugs and reagents as tested on animals. These reagents exhibit the same characteristics as known radiopharmaceuticals such as technetium-99m and iodine-131.

TEST KITS

Radiopharmaceutical kits are well-known in the art and composed of sterile, nonpyrogenic, nonradioactive carrier materials easily activated by the aseptic addition of a radioisotope. For example, one commercially available kit consists of a tin-MDP preparation in the form of a sterile, nonpyrogenic lyophilized powder. Vials containing this powder are suitable for reconstitution with Na$^{99m}$TcO$_4$ to form $^{99m}$Tc-MDP. This kit contains 10 mg MDP and 0.85 mg stannous chloride dihydrate whose pH has been adjusted to pH 7.0–7.5. Vial contents are stored under nitrogen to inhibit stannous oxidation.

EXAMPLE

A variety of tin-117m reagents were administered intravenously to mice, rats, dogs, and rabbits. Table 1 and Table 2 show the types of reagents tested, and the results for mice. Tin-117m-labeled chelates of stannic tin when the chelates were MDP, PYP, EHDP, and DTPA exhibit the greatest localization and bone uptake in combination with the lowest distribution in blood, liver, and kidneys. The preferred reagent is Tin(IV)-117m-DTPA.

TABLE 1

Tissue Distribution in Mice of Various Tin-117m-Labeled Compounds, % Dose per Gram (n = 4)

| Compound | Time after injection | Blood | Bone | Liver | Kidneys | % Dose remaining in whole body |
|---|---|---|---|---|---|---|
| Sn$^{2+}$—chloride, pH2 | 30 min | 18.90 | 18.70 | 6.41 | 15.30 | 101.8 |
|  | 24 hr | 9.04 | 20.90 | 3.99 | 5.03 | 68.4 |
|  | 7 d | 5.64 | 21.80 | 4.62 | 2.21 | 60.8 |
| Sn$^{2+}$—chloride, pH7 | 30 min | 0.09 | 0.87 | 57.40 | 0.62 | 100* |
|  | 24 hr | 0.08 | 1.57 | 61.10 | 0.31 | 100 |
|  | 7 d | 0.17 | 5.20 | 50.40 | 1.58 | 100 |
| Sn$^{4+}$—chloride, pH2 | 30 min | 0.23 | 1.74 | 60.00 | 0.60 | 101.0 |
|  | 24 hr | 0.05 | 3.36 | 52.70 | 0.49 | 89.5 |
|  | 7 d | 0.10 | 7.26 | 28.90 | 1.11 | 62.4 |
| Sn$^{2+}$—MDP | 30 min | 2.77 | 12.80 | 3.39 | 7.37 | 48.7 |
|  | 24 hr | 1.30 | 10.50 | 2.24 | 2.19 | 33.0 |
|  | 7 d | 0.45 | 11.90 | 1.74 | 0.73 | 28.8 |
| Sn$^{4+}$—MDP | 30 min | 0.20 | 16.70 | 1.85 | 0.61 | 41.8 |
|  | 24 hr | 0.02 | 17.70 | 1.37 | 0.50 | 36.6 |
|  | 7 d | 0.01 | 13.90 | 0.91 | 0.33 | 31.0 |
| Sn$^{2+}$—DTPA | 30 min | 7.52 | 10.80 | 4.38 | 7.62 | 59.1 |
|  | 24 hr | 3.77 | 12.30 | 3.03 | 3.03 | 42.2 |
|  | 7 d | 1.15 | 10.80 | 2.08 | 0.92 | 31.7 |
| Sn$^{4+}$—DTPA | 30 min | 0.41 | 19.50 | 0.51 | 1.63 | 45.5 |
|  | 24 hr | 0.01 | 21.50 | 0.30 | 0.44 | 41.8 |
|  | 7 d | 0.01 | 16.70 | 0.19 | 0.23 | 34.5 |
| Sn$^{2+}$—PYP | 30 min | 8.40 | 9.24 | 7.13 | 19.50 | 72.9 |
|  | 24 hr | 3.25 | 12.00 | 5.52 | 2.59 | 40.4 |
|  | 7 d | 0.61 | 12.20 | 2.81 | 0.57 | 29.4 |
| Sn$^{4+}$—PYP | 30 min | 0.33 | 9.81 | 1.94 | 1.36 | 37.1 |
|  | 24 hr | 0.01 | 10.70 | 1.52 | 0.63 | 27.7 |
|  | 7 d | — | 8.74 | 1.15 | 0.30 | 21.6 |
| Sn$^{2+}$—EHDP | 30 min | 3.39 | 12.50 | 3.06 | 9.64 | 64.1 |
|  | 24 hr | 2.26 | 12.20 | 1.97 | 2.41 | 34.3 |
|  | 7 d | 0.84 | 12.60 | 1.36 | 0.59 | 26.2 |
| Sn$^{4+}$—EHDP | 30 min | 0.26 | 9.13 | 0.16 | 0.78 | 25.5 |
|  | 24 hr | — | 9.75 | 0.08 | 0.48 | 19.4 |
|  | 7 d | — | 7.62 | 0.08 | 0.21 | 16.1 |
| $^{99m}$Tc-MDP | 30 min | 0.41 | 11.80 | 1.41 | 1.46 | 33.5 |
|  | 3 hr | 0.14 | 12.30 | 0.97 | 1.11 | 30.2 |
|  | 24 hr | 0.05 | 10.30 | 0.73 | 0.57 | 22.5 |

*Percent dose remaining in whole body normalized to 100 at all time periods.

TABLE 2

Bone to Tissue Ratios in Mice of Various Tin-117m-Labeled Compounds (n = 4)

| Compound | Time after injection | Blood | Muscle | Kidney | Liver |
|---|---|---|---|---|---|
| Sn$^{2+}$—chloride, pH2 | 30 min | 1.0 | .28 | 1.2 | 2.9 |
|  | 24 hr | 2.3 | 123 | 4.2 | 5.2 |
|  | 7 d | 3.9 | 138 | 9.9 | 4.7 |
| Sn$^{2+}$—chloride, pH7 | 30 min | 10 | 16 | 1.4 |  |
|  | 24 hr | 21 | 71 | 5.0 |  |
|  | 7 d | 31 | 133.0 | 3.3 | 0.1 |
| Sn$^{4+}$—chloride, pH2 | 30 min | 7.5 | 21 | 2.9 | 0.03 |
|  | 24 hr | 70 | 121 | 6.9 | 0.06 |
|  | 7 d | 72 | 225 | 6.5 | 0.25 |
| Sn$^{2+}$—MDP | 30 min | 4.6 | 43 | 1.7 | 3.8 |
|  | 24 hr | 8.1 | 333 | 4.8 | 4.7 |
|  | 7 d | 27 | 522 | 16 | 6.8 |
| Sn$^{4+}$—MDP | 30 min | 84 | 99 | 28 | 9 |
|  | 24 hr | 1135 | 460 | 36 | 13 |
|  | 7 d | 1611 | 491 | 42 | 15 |
| Sn$^{2+}$—DTPA | 30 min | 1.4 | 27 | 1.4 | 2.5 |
|  | 24 hr | 3.3 | 91 | 4.1 | 4.1 |
|  | 7 d | 9.4 | 148 | 12 | 5.2 |
| Sn$^{4+}$—DTPA | 30 min | 48 | 77 | 12 | 38 |
|  | 24 hr | 1903 | 863 | 49 | 72 |
|  | 7 d | 2203 | 2489 | 72 | 90 |
| Sn$^{2+}$—PYP | 30 min | 1.1 | 31 | 0.5 | 1.3 |
|  | 24 hr | 3.7 | 79 | 4.6 | 2.2 |
|  | 7 d | 20 | 201 | 22 | 4.3 |
| Sn$^{4+}$—PYP | 30 min | 30 | 39 | 7.2 | 5.1 |
|  | 24 hr | 1144 | 301 | 17 | 7.0 |
|  | 7 d | 5986 | 575 | 29 | 7.6 |
| Sn$^{2+}$—EHDP | 30 min | 3.7 | 40 | 2.3 | 4.1 |
|  | 24 hr | 5.4 | 134 | 5.7 | 6.2 |
|  | 7 d | 15 | 380 | 21 | 9.3 |
| Sn$^{4+}$—EHDP | 30 min | 35 | 115 | 12 | 56 |
|  | 24 hr | 2928 | 210 | 20 | 122 |
|  | 7 d | 10000 | 1383 | 36 | 106 |
| $^{99m}$Tc-MDP | 30 min | 29 | 93 | 8.1 | 8.4 |
|  | 3 hr | 85 | 270 | 11 | 13 |
|  | 24 hr | 205 | 375 | 18 | 14 |

We claim:

1. A radiopharmaceutical composition consisting of Tin-117m-labeled Stannic (Sn$^{4+}$)-chelate in which the chelate component is a chelant selected from the group consistency of methylene diphosphonate (MDP), pyrophosphate (PYP), ethylidenehydroxydisodium phosphonate (EHDP) and diethylinetriaminopentaacetic acid (DTPA).

2. A radiopharmaceutical composition consisting of tin-117m-Stannic (Sn$^{4+}$)-DTPA.

3. A method of preparing bone for scintigraphical analysis consisting of administering a scintigraphically acceptable amount of chelate tagged with tin-117m in Stannic (Sn$^{4+}$) form.

4. A method for radiopharmaceutical skeletal imaging comprising administering intravenously tin-117m-labeled Stannic (Sn$^{+4}$) chelate reagent and detecting the tin-117m by gamma scintigraphy or a whole body scan.

5. A method of monitoring a mammalian skeletal system comprising intravenously administering a tin-117m-labeled Stannic (Sn$^{4+}$) chelate reagent and measuring by scintigraphy the distribution of the chelate throughout the body and its localization on bone.

* * * * *